(12) United States Patent
Gruczynski et al.

(10) Patent No.: US 11,478,357 B2
(45) Date of Patent: Oct. 25, 2022

(54) MODULAR POLYMER FEMORAL COMPONENTS WITH METALLIC INSERTS

(71) Applicant: Howmedica Osteonics Corp., Mahwah, NJ (US)

(72) Inventors: Mark Gruczynski, Kinnelon, NJ (US); Keenan Michael Hanson, Sloatsburg, NY (US)

(73) Assignee: Howmedica Osteonics Corp., Mahwah, NJ (US)

( * ) Notice: Subject to any disclaimer, the term of this patent is extended or adjusted under 35 U.S.C. 154(b) by 196 days.

(21) Appl. No.: 16/897,668

(22) Filed: Jun. 10, 2020

(65) Prior Publication Data

US 2021/0059826 A1 Mar. 4, 2021

Related U.S. Application Data

(60) Provisional application No. 62/891,501, filed on Aug. 26, 2019.

(51) Int. Cl.
*A61F 2/38* (2006.01)
*A61F 2/30* (2006.01)

(52) U.S. Cl.
CPC ........ *A61F 2/3859* (2013.01); *A61F 2/30767* (2013.01); *A61F 2002/3093* (2013.01);
(Continued)

(58) Field of Classification Search
CPC .............. A61F 2/3859; A61F 2/30767; A61F 2002/30574; A61F 2002/3093; A61F 2002/3863; A61F 2002/3895; A61F 2002/30011; A61F 2002/30329; A61F 2002/30383; A61F 2002/30385; A61F 2002/30477; A61F 2002/305; A61F 2002/30604; A61F 2002/3069; A61F 2002/30878; A61F 2002/30971;
(Continued)

(56) References Cited

U.S. PATENT DOCUMENTS 4,950,298 A 8/1990 Gustilo et al.
9,168,155 B2 10/2015 Earl et al.
(Continued)

FOREIGN PATENT DOCUMENTS

WO 2004078074 A1 9/2004

*Primary Examiner* — Jerrah Edwards
*Assistant Examiner* — Jared Klar Rovira
(74) *Attorney, Agent, or Firm* — Lerner, David, Littenberg, Krumholz & Mentlik, LLP

(57) ABSTRACT

A system for converting a first joint prosthesis to a second joint prosthesis in-situ includes a plurality of inserts having a bone interface side and a component facing side and a plurality of articulating components having a cavity configured to receive at least one of the plurality of inserts. The plurality of inserts may be unicompartmental, bicompartmental, or tricompartmental. The inserts may be made of metal and may have a bone contacting surface made of a porous metal. The plurality of articulating components may be unicompartmental, bicompartmental, or tricompartmental. The articulating components may be sized and shaped to cover one or more of the plurality of bone interface components and span a distance therebetween. The articulating components may be made of a polymer.

18 Claims, 7 Drawing Sheets

(52) U.S. Cl.
CPC ............ *A61F 2002/30574* (2013.01); *A61F 2002/3863* (2013.01); *A61F 2002/3895* (2013.01)

(58) Field of Classification Search
CPC ...... A61F 2002/4619; A61F 2002/4622; A61F 2002/4625; A61F 2002/4627; A61F 2002/4628; A61F 2002/4641; A61F 2/3877; A61F 2/4603; A61F 2/461; A61F 2/4637
See application file for complete search history.

(56) References Cited

U.S. PATENT DOCUMENTS

| | | |
|---|---|---|
| 10,219,908 B2 | 3/2019 | Nadzadi et al. |
| 2006/0190086 A1* | 8/2006 | Clemow ................ A61F 2/38 623/20.15 |
| 2009/0125115 A1 | 5/2009 | Popoola et al. |

* cited by examiner

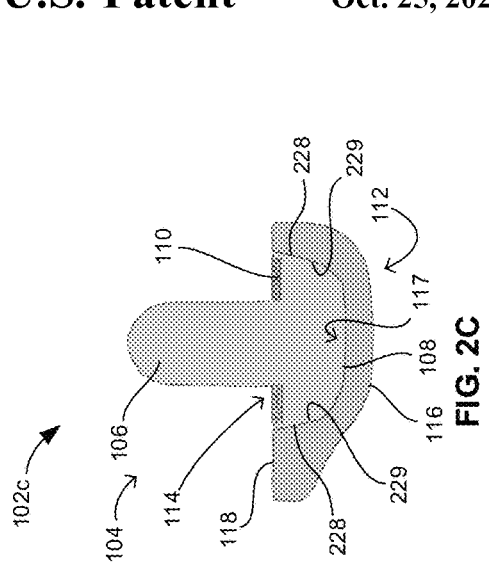
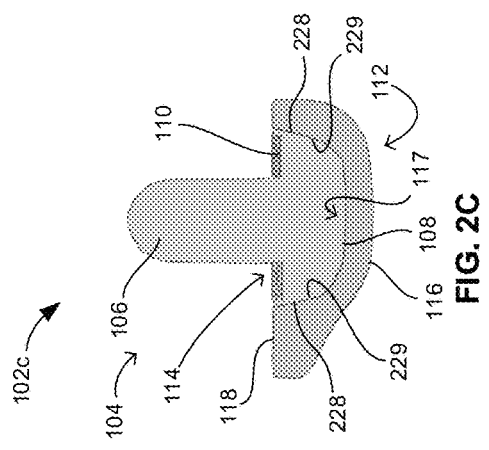
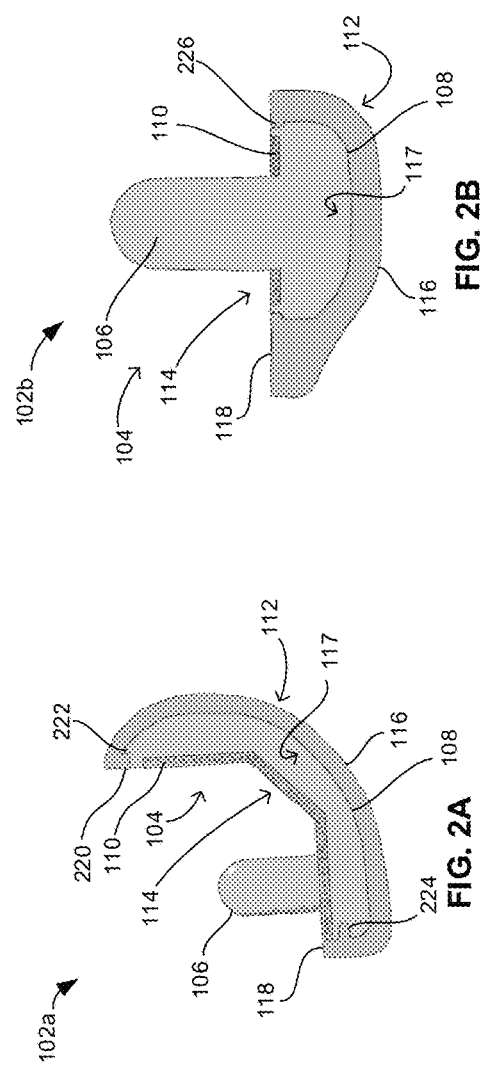
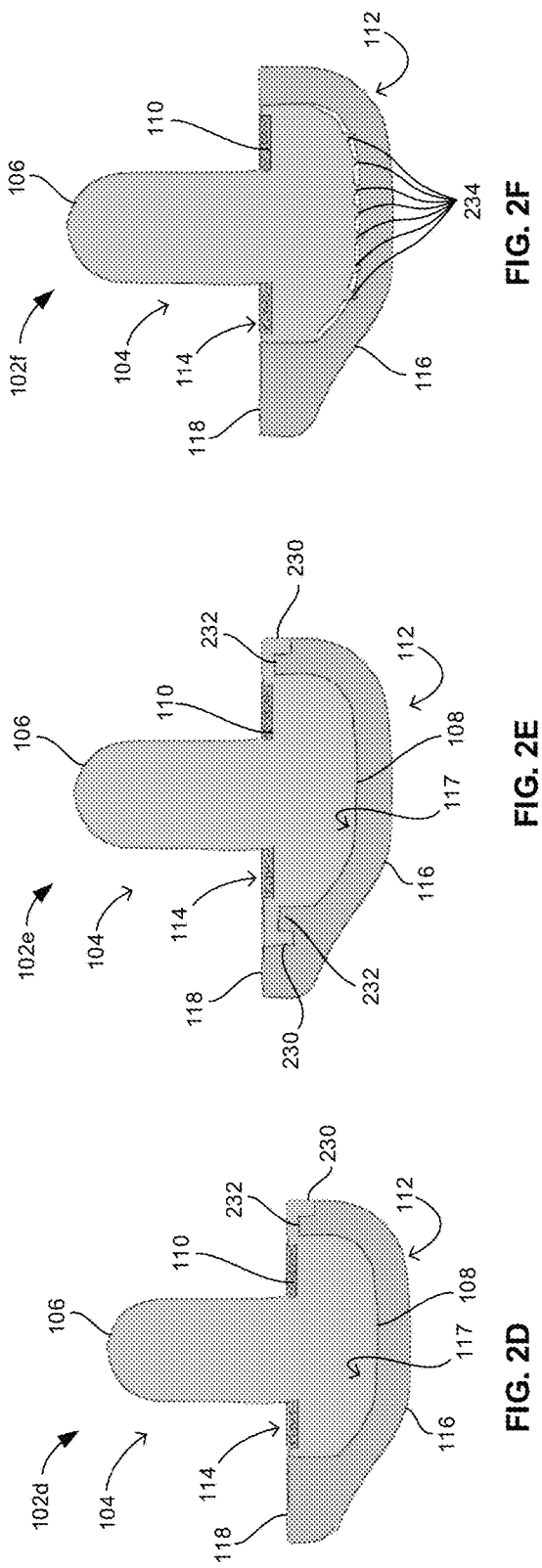
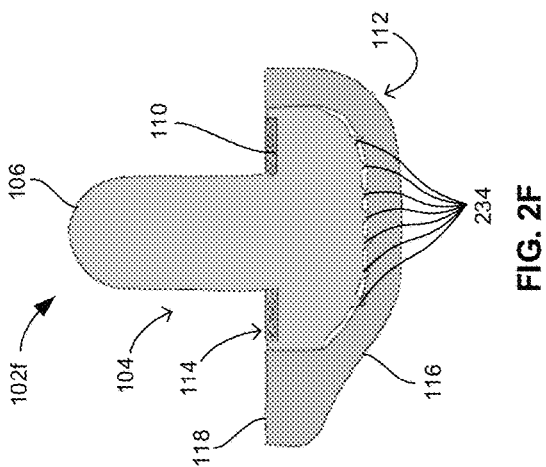
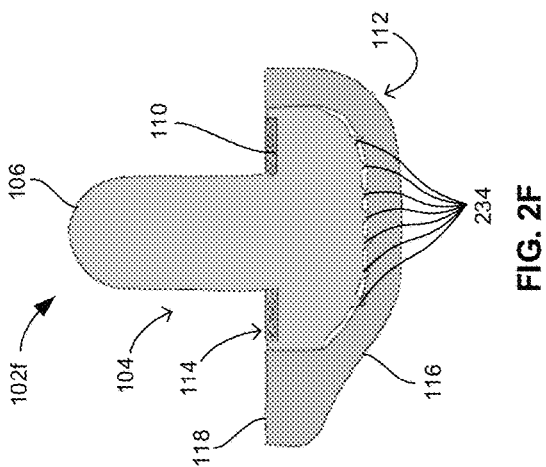

MODULAR POLYMER FEMORAL COMPONENTS WITH METALLIC INSERTS

CROSS-REFERENCE TO RELATED APPLICATIONS

The present application claims the benefit of the filing date of U.S. Provisional Patent Application No. 62/891,501, filed Aug. 26, 2019, the disclosure of which is hereby incorporated herein by reference.

The current state of the art in knee replacement surgery offers orthopedic surgeons with a myriad of options to treat their patients, depending on the specific condition to be treated. The vast majority of knee replacement surgery is to treat arthritis of the knee, with trauma and bone cancer being exceptions. Knee replacement surgery to treat arthritis of the knee varies significantly depending on the state of disease progression.

The knee joint consists generally of three distinct regions, the medial tibiofemoral compartment, the lateral tibiofemoral compartment and the patellofemoral compartment. Arthritis of the knee can be limited to one compartment, for example the patellofemoral compartment or the medial tibiofemoral compartment. Conversely, arthritis can be found in two compartments simultaneously, for example the patellofemoral and medial tibiofemoral compartments. Finally arthritis can be found in all three aforementioned compartments.

Knee replacement surgery can be tailored to treat the specific condition diagnosed. For example, for patients with isolated compartmental disease, a partial knee replacement or partial knee arthroplasty ("PKA") procedure may be performed, such as a unicompartmental or bicompartmental knee replacement. In patients with arthritis in all three compartments, a total joint knee replacement or total knee arthroplasty ("TKA") may be performed.

Patients who undergo primary knee replacement surgery, whether for a PKA or a TKA, can expect to undergo one or more revision procedures. The causes that frequently necessitate such revision surgery can vary from mechanical failure of the implant to further disease progression. For example, a patient who undergoes a PKA procedure to replace arthritic bone within less then all three compartments of a knee joint may undergo a revision procedure to address arthritis that develops after the PKA procedure in the remaining native compartment or compartments.

However, an issue generally encountered by surgeons replacing joints during a revision procedure is the additional loss of native bone near the joint being replaced. This bone loss may be caused by the removal of a well affixed, previously implanted prosthesis. In this regard, prosthetic components are typically cemented to bone or utilize porous surfaces that promote bone growth into the prosthesis. As such, the removal of a well affixed prosthesis often involves the removal of bone at the prosthesis interface when the prosthesis is removed. Thus, the remaining bone may not be suitable for connection to a revision prosthesis and may, therefore, need to be resurfaced which requires further removal of bone.

Therefore, there exists a need for an improved system of implants for use in TKA and/or PKA procedures.

BRIEF SUMMARY OF THE INVENTION

In a first aspect of the present disclosure, a method of converting a first joint prosthesis to a second joint prosthesis in-situ include removing a first articulating component from a first bone interface component having been connected to a bone in a previous procedure such that the first interface component remains connected to the bone. A second bone interface component is connected to a resected portion of the bone. The first bone interface component and the second bone interface component are connected via a second articulating component, wherein the second articulating component is sized and shaped to cover both the first and second bone interface components and span a distance therebetween. The first and second bone interface components may be made of a metal. The first and second bone interface components may each include a bone contacting surface made of a porous metal. The first and second articulating components may be made of a polymer.

Additionally, the method may include implanting a third bone interface component to the resected portion of the bone. The third bone interface component may be connected to the first and second bone interface components via the second articulating component, wherein the second articulating component is sized and shaped to cover each of the first, second, and third bone interface components. The second articulating component may be a tricompartmental femoral component that includes lateral and medial condyles for tibiofemoral articulation and an anterior flange having a trochlear groove for patellofemoral articulation. Alternatively, the second articulating component may be a bicompartmental femoral component that includes an anterior flange defining a trochlear groove for patellofemoral articulation and either a lateral or medial condyle for unicondylar tibiofemoral articulation.

Continuing with this aspect, the step of removing the first articulating component may further comprise cutting the first articulating component at a location adjacent to a locking mechanism, the locking mechanism coupling the first articulating component to the first bone contacting component. The step of connecting the first bone interface component and the second bone interface component may further include applying a force to the second articulating component to deform the second articulating component to snap-fit the second articulating component onto one or more locking mechanisms on the first and second bone interface components.

In another aspect of the present disclose, a method of converting a first joint prosthesis to a second joint prosthesis in-situ includes removing a first articulating component from a first bone interface component such that the first bone interface component remains attached to a femur, the first bone interface component having been previously connected to the femur in a previous procedure. A second bone interface component may be connected to a resected portion of the femur and a second articulating component may be connected to the first and second bone interface components.

The first articulating component may include a unicondylar component that has an articular surface that defines one of a lateral and medial condyle. Additionally or alternatively, the first articulating component may include a patellofemoral component that has an articular surface that defines a trochlear groove for patellofemoral articulation. The second articulating component may include a unicondylar component and a patellofemoral component such that the second articulating component is a bicompartmental component. The step of connecting the second articulating component to the first and second bone interface components may include connecting the tibiofemoral component to the first or second bone interface component and connecting the unicondylar component to the other of the first and second bone interface components such that the unicondylar component and patellofemoral component are spaced apart from each other.

Continuing with this aspect, the method may further include connecting a third bone interface component to the femur such that the first, second, and third bone interface components are each spaced apart from one another. The second articulating component may be connected to the third bone interface component. The second articulating component may be a full-articulation tricompartmental component having lateral and medial condyles for tibiofemoral articulation and an anterior flange defining a trochlear groove for patellofemoral articulation. Alternatively, the second articulating component includes first and second unicondylar components and a patellofemoral component. The step of connecting the second articulating component to the first, second, and third bone interface components may include separately connecting the first and second unicondylar components and patellofemoral component to any of the first, second, and third bone interface components not occupied by one of the other unicondylar or patellofemoral components. The removing step may include cutting off a portion of the first articulating component from the first bone interface component.

In a further aspect of the present disclosure, a system for converting a first joint prosthesis to a second joint prosthesis in-situ includes a first unicompartmental insert having a bone interface side and a component facing side, a second unicompartmental insert having a bone interface side and a component facing side, and an articulating component having a cavity configured to receive both of the first and second unicompartmental inserts therein. The first and second unicompartmental inserts and articulating component may each define a connection mechanism configured to secure the articulating component to the first and second unicompartmental inserts.

BRIEF DESCRIPTION OF THE DRAWINGS

The features, aspects, and advantages of the present disclosure will become better understood with regard to the following description, appended claims, and accompanying drawings in which:

FIGS. 2A-2F are cross-sectional views of various connection means between the insert and the articulating component of FIG. 1A.

DETAILED DESCRIPTION

When referring to specific directions in the following discussion of certain implantable devices, it should be understood that such directions are described with regard to the implantable device's orientation and position during exemplary application to the human body. Thus, as used herein, the term "proximal" means close to the heart, and the term "distal" means more distant from the heart. The term "inferior" means toward the feet, and the term "superior" means toward the head. The term "anterior means toward the front of the body or the face, and the term "posterior" means toward the back of the body. The term "medial" means toward the midline of the body, and the term "lateral" means away from the midline of the body. Also, as used herein, the terms "about," "generally" and "substantially" are intended to mean that slight deviations from absolute are included within the scope of the term so modified.

Figure 1A:
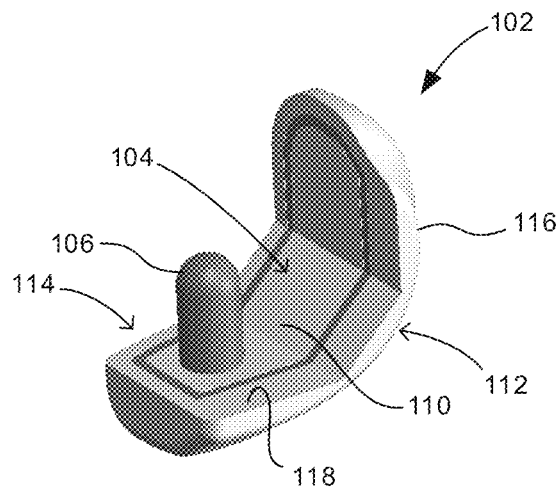
FIG. 1A is a perspective view of an implant according to an embodiment of the present disclosure including an insert and an articulating component.
Figure 1B:
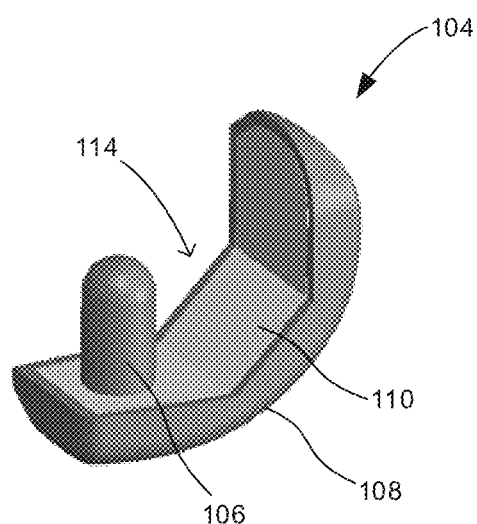
FIG. 1B is a perspective view of the insert of FIG. 1A.

FIGS. 1A-1B depict an implant 102 according to one embodiment of the present invention. Implant 102 includes a bone interface component or insert 104 and an articulating component 112. Implant 102, according to the depicted embodiment, is a unicompartmental implant and, more specifically, a unicondylar implant. Implant 102 is discussed below as being used as either a medial or lateral condylar implant. There are typically some structural differences between medial and lateral condylar implants to account for their particular application to a medial or lateral side of a knee. However, for the purposes of this disclosure, implant 102 is representative herein of both a medial and a lateral unicondylar implant and will appear herein substantially the same whether it is being used on the medial or lateral side of the knee.

Insert 104 has a bone contacting surface 114. Opposite to bone contacting surface 114 is an articulating component mating or facing surface 108. Bone contacting surface 114 has a profile configured to match the profile of a resected femur. Thus, the profile of bone contacting surface 114 may be configured for a curved bone cut, such as may be produced by a robotic device or a mechanically guided milling tool, or planar bone cuts as may be produced by standard manual instrumentation. For example, a femur may be resected with three planar bone cuts or five planar bone cuts. Bone contacting surface 114, thus, can include various geometries to match that of a resected femur. For example, bone contacting surface 114 may have a concavely curved surface to match that of a convexly curved resected femur. In another example, bone contacting surface 114 may have two or more intersecting planar surfaces to correspond to planar surfaces of a resected femur. Some additional exemplary bone interface configurations, including planar and curved bone cuts, are described in U.S. Pat. No. 10,219,908 titled "Femoral Component for Bone Conservation," which is hereby incorporated by reference herein in its entirety.

As shown in FIG. 1B, bone contacting surface 114 has three (3) planar surfaces to correspond to three planar resected surfaces of a femur. Extending from one of the planar surfaces of bone contacting surface 114 is a peg or protrusion 106. Protrusion 106, as shown, extends away from bone contacting surface 114 and is generally cylindrical. Protrusion 106 may include a domed surface at the end furthest away from bone contacting surface 114. Protrusion 106 is configured to be inserted into a corresponding recess in the resected femur as a means to attach, connect, or couple insert 104 to the resected femur (as shown in FIGS. 6A-6E).

The thickness of insert 104 can be varied to better match the mechanical characteristics of the femur. For example, insert 104 may be thinner for an early stage intervention as compared to a revision procedure. Nonetheless, insert 104 is preferably thick enough to prevent deformation of bone contacting surface 114 so that bone contacting surface 114 does not inadvertently separate from the underlying bone. While not shown, insert 104 may include additional features, such as ribs or keels, to increase the stiffness of insert 104. Insert 104 may be made of a biocompatible material, such as a biocompatible metal or polymer. However, insert 104 is preferably made from a biocompatible metal, such as titanium, stainless steel, cobalt-chromium, niobium, tantalum, and the like. In addition, at least a portion of the bone contacting surface 114 of insert 104 comprises a porous structure 110 to promote bone ingrowth into the porous structure 110.

Articulating component 112 has an articulating surface 116. Opposite articulating surface 116 is a bone contacting surface 118. As shown, bone contacting surface 118 may be correspondingly contoured relative to that of bone contacting surface 114 of insert 104. As such, where bone contacting surface 114 includes a plurality of intersecting planar surfaces, articulating component 112 may include similar intersecting planar surfaces. In this regard, articulating component 112 is configured to connect, or couple, to insert 104 such that bone contacting surface 114 of insert 104 aligns with the bone contacting surface 118 of articulating component 112. To facilitate such connection between articulating component 112 and insert 104, a cavity or insert void 117 extends into bone contacting surface 118. Such recess 117 has a shape that conforms to a peripheral shape of insert 104 and is configured to receive insert 104 therein. As a result, articulating component 114 covers insert 104 so that insert 104 is housed therein. Thus, articulating component 112 may, at least, partially encompass insert 104 such that articulating component surface 108 is covered. Articulating component 112 is preferably made of a biocompatible polymer, such as polyether ether ketone (PEEK), such that articulating component is durable yet flexible. While not shown, articulating component 112 may include at least one tab or a feature, such as indicia on a surface within recess 117, to distinguish between left and right implants and medial and lateral condyles. Insert 104 may have a corresponding cutout or recess to receive the tabs so that only like inserts 104 can couple with like articulating components 112.

FIGS. 2A-2F illustrate various means for connecting, coupling, securing, anchoring or attaching articulating component 112 to insert 104. The connecting means may include one or more locking mechanisms to connect, couple, secure, anchor, or attach articulating component 112 to insert 104.

FIG. 2A depicts an implant 102a that provides for a snap-fit mechanism to secure insert 104 with articulating component 112. In such embodiment, insert 104 includes a protrusion or flange 222 which may be created by a recess or notch in bone contacting surface 114 of insert 104 at one end thereof. Moreover, articulating component 112 may include a lip 220 configured to engage protrusion 222. Insert 104 may also include a groove or recess at another end thereof that is sized and shaped to receive a protrusion 224 of articulating component 112. Protrusion 222, lip 220, projection 224, and its corresponding groove can be at any location around the perimeter of insert 104 and articulating component 112.

An external force by hand or specialized instrument elastically deforms articulating component 112 to snap-fit articulating component 112 around insert 104, which can be performed in-situ. Articulating component 112 may begin in a neutral position and, thereafter, be elastically deformed such that the space and/or distance between the opposing ends of articulating component 112 is increased. Elastic deformation includes material elongation of articulating component 112. The elastic deformation allows for protrusion 224 and lip 220 to be aligned with the corresponding groove and protrusion 222, respectively, on insert 104, such that these mating parts snap-fit together to anchor articulating component 112 to insert 104. When the external elastic deformation force is removed, compressive forces acting around insert 104 anchor articulating component 112 to insert 104. In addition to the compressive force created by articulating component 112, the interlocking engagement features on insert 104 (i.e., protrusion 222 and the groove corresponding to projection 124) and the engagement features of articulating component 112 (i.e., protrusion 224 and lip 220) results in a snug fit and a strong bond. Once articulating component 112 is anchored to insert 104, articulating component 112 covers one side of insert 104 while the other side mates with a bone.

FIG. 2B depicts implant 102b which illustrates another snap-fit connection means between insert 104 and articulating component 112. Much like the snap-fit connection means illustrated in FIG. 2A, articulating component 112 includes lip 226. Lip 226 may extend around the entire inner perimeter of articulating component 112 such that lip projects inward toward cavity 117. According to some embodiments, lip 226 may only extend around a portion of the inner perimeter of articulating component 112. Insert 104 may have a corresponding recess or groove in bone contacting surface 114 at an edge thereof configured for receipt of lip 226, as shown. Articulating component 112 may be attached to insert 104 in a similar fashioned as the method described with respect to FIG. 2A. In other words, articulating component 112 may be deformed via an external force to snap-fit onto insert 104, which may occur in-situ while insert 104 is connected to a bone.

FIG. 2C depicts implant 102c which illustrates a press-fit taper-lock connection between insert 104 and articulating component 112. In this regard, insert 104 includes tapered exterior side surfaces 228, and articulating component 112 includes correspondingly tapered inner side surfaces 229. However, the distance between side surfaces 229 of articulating component 112 may be slightly smaller than that of insert 104 so as to create an interference when insert 104 is coupled to articulating component 112 in order to achieve the taper-lock. While only illustrated in FIG. 2C, tapered surfaces 228, 229 may be included in addition to any of the other connection mechanisms described herein, such that tapered surfaces 228, 229 provide additional connection means.

FIGS. 2D and 2E depict implants 102d and 102e, respectively, which illustrate a rail mechanism as a means for anchoring articulating component 112 to insert 104. FIG. 2D includes a single rail 230 on one side of implant 102, whereas FIG. 2E includes two rails 230, one on each side of implant 102. Rails 230 are formed as an extension of insert 104 and are, therefore, integral to insert 104. In addition, rails 230 extend outwardly and downwardly in a direction toward component facing surface 108 so as to define an "L" shape with a corresponding groove located between each rail 230 and the bulk of insert 104. Articulating component also has rails 232 and grooves that are configured to mate with the rails 230 and grooves of insert 104 in an overlapping manner. However, rails 230, 232 may be slightly larger than their corresponding groove so as to form a press-fit when mated together. Alternatively, the rails 230, 232 and grooves may be correspondingly tapered so that they form a taper lock when mated together.

FIG. 2F illustrates another connection means for connecting articulating component 112 to insert 104. As shown, insert 104 may include protrusions or projections, such as spikes 234, which can create a friction fit between insert 104 and articulating component 112. Spikes 234 may be integral to insert 104, such that spikes 234 are formed of metal. Spikes 234 include sharp or pointed tips that can dig or embed themselves into the polymer of articulating component 112. Spikes 234 may prevent anterior-posterior and/or medial-lateral motion between insert 104 and articulating component 112. While spikes 234 are shown on their own, without the addition of another connection means, spikes 234 can be used in conjunction with any of the connection means described herein.

While not shown, external fasteners, such as screws and locking wire can be used to provide an additional anchoring mechanism between insert 104 and articulating component 112.

When the need arises to replace a worn articulating component or convert from a PKA to a TKA, insert 104 is configured to remain in place when articulating component 112 is removed. For example, a revision procedure may include the conversion from a unicompartmental implant to a bicompartmental implant. In another example, a revision procedure may include the conversion of a unicompartmental or bicompartmental implant t to a tricompartmental implant. In a further example, a revision procedure may include the replacement of a worn articulating component, such as component 112, without increasing the number of artificial compartments. In all cases, a previously implanted insert 104 would remain and, if necessary, only articulating component 112 would be removed to perform a replacement or revision surgery. This may provide for a more stable overall implant as insert 104 will have become anchored into the femur due to the bone ingrowth into the porous metal on bone contacting surface 114. Moreover, more healthy bone remains, as less bone may have to be resected to prepare the femur for additional or replacement inserts and/or articulating components.

Figure 3B:
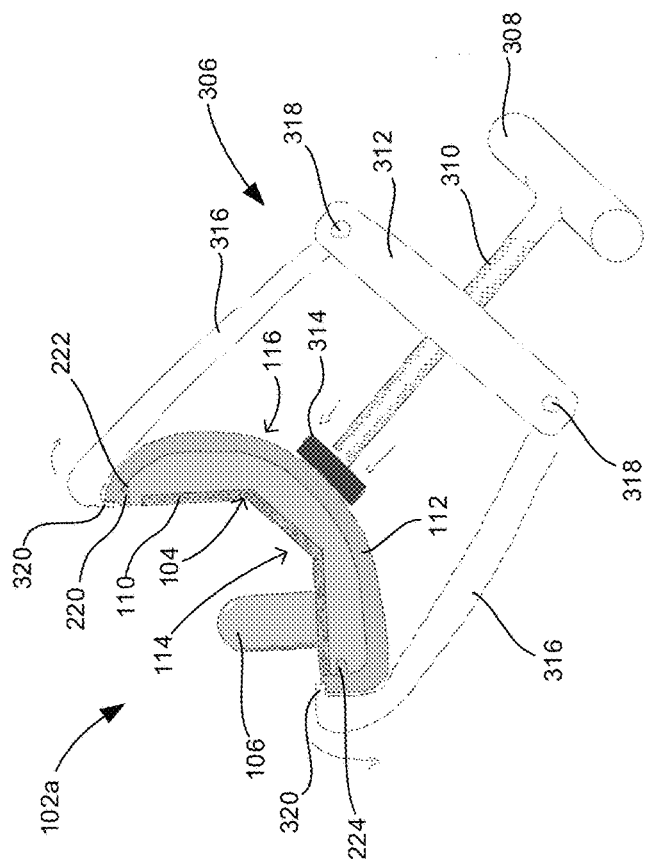
FIG. 3B depicts a method of removal of the articulating component from the insert of FIG. 2A according to another embodiment of the present invention.
Figure 3A:
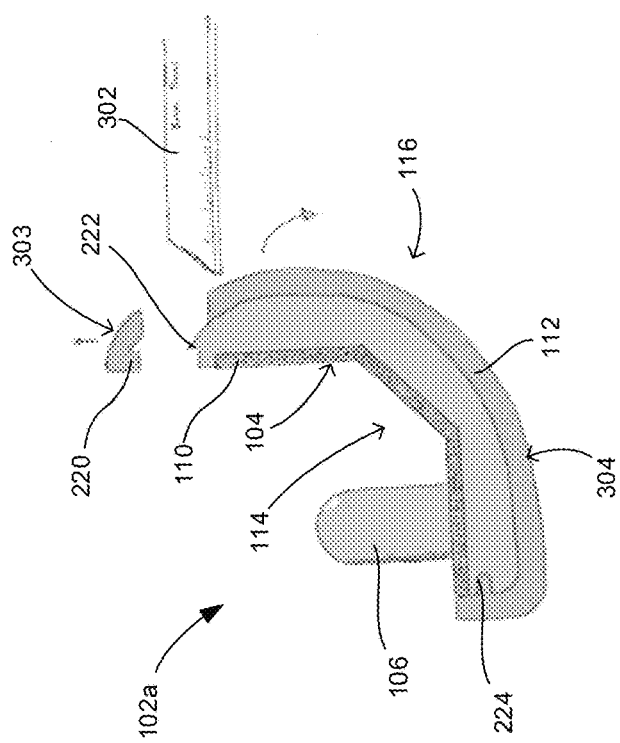
FIG. 3A depicts a method of removal of the articulating component from the insert of FIG. 2A according to one embodiment of the present invention.

FIGS. 3A and 3B illustrate two means of removing articulating component 112 so that another articulating component can be secured to insert 104. As shown in FIG. 3A, a saw 302 is used to cut articulating component 112 at or near protrusion 222 such that portion 303 of articulating component 112 including lip 220 is detached from the body portion 304 of articulating component 112. Thus, saw 302 is used to cut through the polymer articulating component 112. While saw 302, such as a bone saw, is illustrated, any cutting means can be used to remove portion 303 of articulating component 112. Moreover, articulating component 112 can be cut at any location that will allow for its removal from insert 104.

The removal of portion 303 of articulating component 112 removes the snap-fit anchoring means between insert 104 and articulating component 112. Thus, body portion 304 of articulating component 112 can be removed from insert 104 without removing or disturbing insert 104 while insert 104 remains connected to underlying bone. Body portion 304 of articulating component 112 can be bent or flexed towards projection 224 such that projection 224 is removed from the corresponding recess in insert 104. Once projection 224 is freed from the corresponding recess in insert 104, body portion 304 of articulating component 112 can be removed from insert 104.

FIG. 3B illustrates an alternative means for removing articulating component 112 from insert 104. Removal tool 306 can be used to remove articulating component 112 from insert 104. Removal tool 306 includes a handle 308, shaft 310, cross bar 312, bumper 314, and arms 316. Shaft 310 may include threads, such that shaft 310 is mated with a threaded throughhole (not shown) in cross bar 312. Handle 308 is connected to or may be integral with shaft 310 at one end of shaft 310 and bumper 314, too, is connected to or may be integral with shaft 310 at the end opposite the handle. Thus, handle 308 may be on one side of cross bar 312 and bumper 314 on the other with shaft 310 extending therebetween. Arms 316 are connected to cross bar 312 using a connection means that allows for arms 316 to rotate around connection point 318.

Removing articulating component 112 using removal tool 306 includes inserting lips 320 of arms 316 into a recess or cutout in articulating component 112 configured for the receipt of lips 320. The recesses or cutouts in articulating component 112 are at both the anterior-superior and the inferior-posterior ends of articulating component 112 (i.e., opposing ends of articulating component 112). Alternatively, lips 320 of arms 316 extend over opposing edges of articulating component 112 without the use of specially configured recesses or cutouts. Once lips 320 are in place on articulating component 112, handle 308 is rotated such that bumper 314 is advanced towards articulating component 112. As bumper 314 presses on articulating component 11, 112, arms 316 will flare outwardly around connection point 318. Thus, as bumper 314 presses on articulating component, lips 320 pull on articulating component 112, such that articulating component 112 flexes or bends freeing lip 220 and protrusion 224 from insert 104. Once lip 220 and protrusion 224 are freed from the corresponding features on insert 104, articulating component 112 is completely removed from insert 104 without disturbing or removing insert 104.

Figure 4:
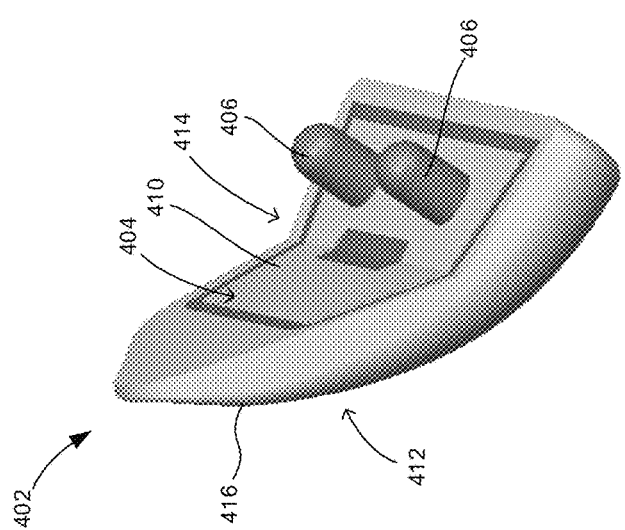
FIG. 4 is a perspective view of an implant according to another embodiment of the present invention.

FIG. 4 illustrates a patellofemoral implant 402, with structure similar to the unicompartmental implant 102 discussed above. Thus, implant 402 includes an insert 404 preferably made of metal and having a bone contacting surface 414. At least a portion of bone contacting surface 414 may be made of a porous structure 410. Alternatively, surface 414 may be nonporous and configured for cemented fixation. Extending from bone contacting surface 414 is at least one projection 406 configured to be received by a corresponding recess in a resected femur. Implant 402 also includes an articulating component 412. Articulating component 412 is preferably made of a polymer, such as PEEK, as described above and has an articulating surface 416.

Articulating surface is configured with a groove 415 (see FIG. 6B), which is configured to articulate with a patella. Insert 404 and articulating component 412 are configured to connect to each other using one of the exemplary means described above such that articulating component 412 can be readily removed and replaced by a similar or different articulating component.

Figure 5A:
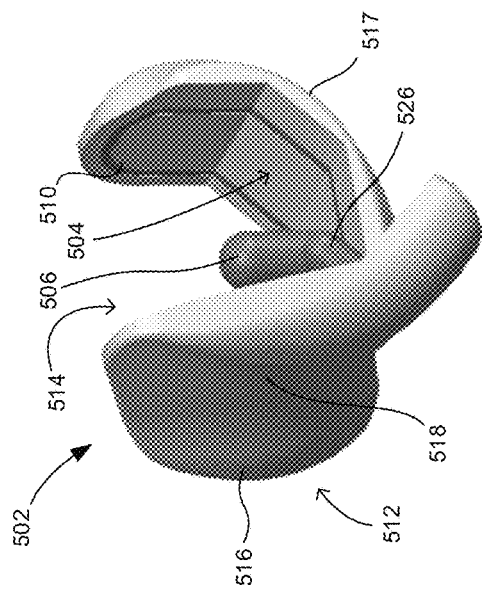
FIG. 5A is a perspective view of an implant according to a further embodiment of the present disclosure including an insert an articulating component.
Figure 5B:
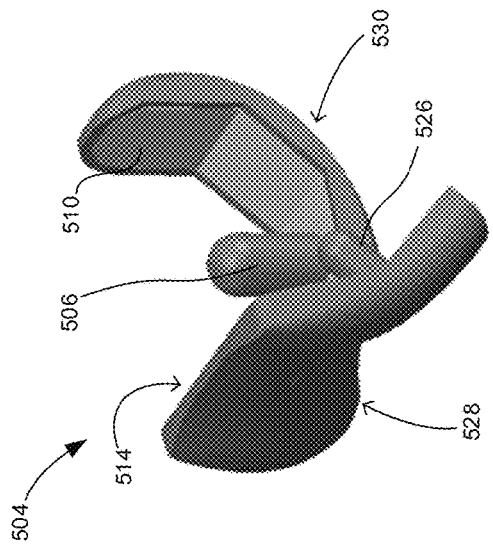
FIG. 5B is a perspective view of the insert of FIG. 5A.

FIGS. 5A and 5B illustrate a bicompartmental implant. Implant 502 includes insert 504 and articulating component 512. Insert 504 includes a first portion 528 that is a patellofemoral insert and a second portion 530 that is a medial condylar insert. However, in some embodiments, second portion 530 may be a lateral condylar insert and, in such embodiments, would be located adjacent to insert 530 as it is depicted in its medial position in FIG. 5B. Thus, as shown, implant 502 is a bicompartmental implant which is comprised of a bicompartmental insert 504. First portion 528 and second portion 530, as shown, are connected to each other such that insert 502 is a monolithic structure comprised of first and second portions 528, 530. Thus, according to some embodiments, portion 530 is connected to portion 528 when each portion 528, 530 is connected to the femur.

However, in some embodiments, as described in more detail below, bicompartmental implant 502 may be comprised of a combination of separate inserts, such as inserts 104 and 404. In such embodiments, inserts 104 and 404 may be separately connected to a bone but may receive articulating component 516 in a similar fashion as insert 504, as described below.

As discussed above with respect to implant 102, insert 504 is preferably made of metal and includes a bone contacting surface 514. At least a portion of bone contacting surface 514 may be made of a porous structure 510. Alternatively, surface 514 may be nonporous and configured for cemented fixation. Extending from bone contacting surface 514 of first portion 528 is projection 506. Also, extending from bone contacting surface 514 of second portion 530 is at least one projection 526. Projections 506, 526 are configured to be received by corresponding recesses in a resected femur to couple insert 504 to the resected femur.

Articulating component 512 is a bicompartmental femoral component that includes an anterior flange portion 516 defining a trochlear groove 518 for patellofemoral articulation and either a lateral or medial condylar portion 530 for tibiofemoral articulation. Similar to insert 504, anterior flange 516 and condylar portion 517 are connected to each other to form a monolithic structure. In addition, articulating component 512 includes a cavity, similar to cavity 117, that is configured receive insert 504 in a manner similar to that described above with respect to implant 102 such that articulating component 512 and insert 504 are connectable and disconnectable in-situ. Thus, insert 504 and articulating component 528 may have a one of the aforementioned connection means to secure articulating component 528 to insert 504 or, alternatively, to inserts 104 and 404.

FIGS. 6A-6E illustrate various unicompartmental and bicompartmental combinations of implants on a resected femur. Femur 600 is shown as resected with five planar bone cuts. However, this is merely illustrative. Femur 600 may have more or less resections and may have resections that are differently contoured, such as convexly curved, as discussed above. Thus, the five-cut femur as shown is merely for viewing ease and does not necessarily reflect the proper resection of femur 600 for the depicted implants. Femur 600 depicts recesses 602 that correspond to protrusions 106, 406, 506, 526 of inserts 104, 404, and 504, respectively. Thus, protrusion 106, 406, 506, 526 can be inserted into the corresponding recess 602 such that the desired insert and corresponding articular component is anchored to femur 600.

Figure 6A:
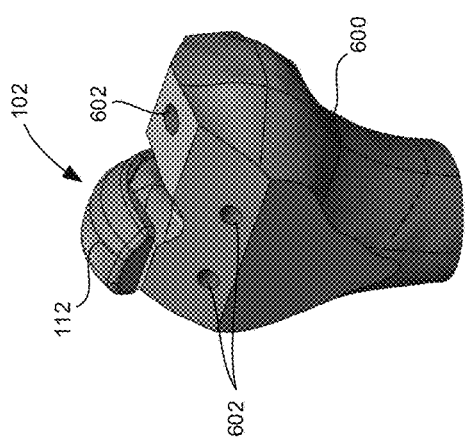
FIG. 6A is a perspective view of the implant of FIG. 1A connected to a medial side of a resected femur.
Figure 6B:
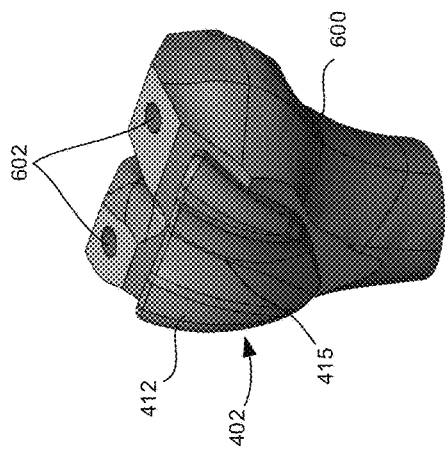
FIG. 6B is a perspective view of the implant of FIG. 4 connected to a resected femur.
Figure 6C:
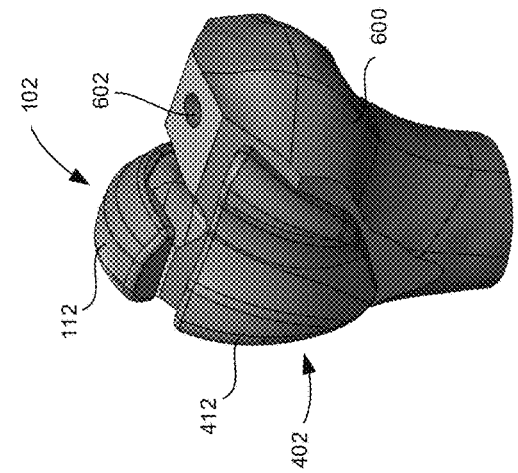
FIG. 6C is a perspective view of both the implant of FIG. 1B and FIG. 4 connected to a resected femur.
Figure 6D:
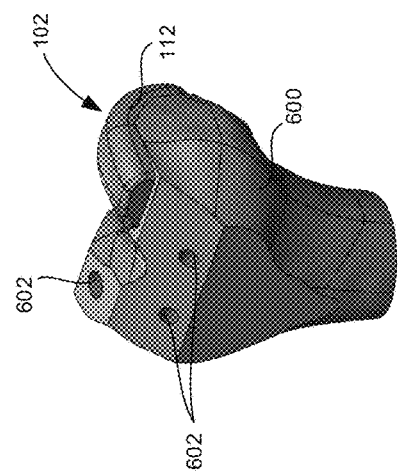
FIG. 6D is a perspective view of the implant of FIG. 1B connected to a lateral side of a resected femur.

FIGS. 6A, 6B, and 6D illustrate various unicompartmental configurations utilizing implant 102 and 402. In particular, FIG. 6A shows implant 102 as a medial condylar implant, and 6D shows implant 102 as a lateral condylar implant. FIG. 6B shows implant 402 as a patellofemoral unicompartmental implant. Thus, in FIGS. 6A and 6D, insert 104 is removably connected to the femur and articular component 112 is connected to insert 104. Similarly, insert 404 is connected to femur in FIG. 6B, while articular component 412 is removably connected to insert 404.

Figure 6E:
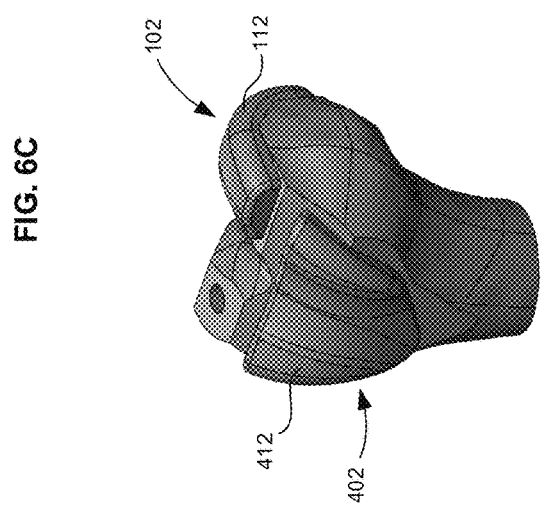
FIG. 6E is a perspective view of both the implant of FIG. 1B and FIG. 4 connected to a resected femur.

FIGS. 6C and 6E illustrate various bicompartmental configurations utilizing implants 102 and 402. In this regard, implant 102 is utilized as a unicondylar implant for either the lateral or medial condyle while implant 402 is utilized as a patellofemoral implant so as to replace two compartments, the patellofemoral compartment and one of the tibiofemoral compartments. Although, not shown, it is also contemplated that implant 102 may be used on both the lateral and medial condyles to form a bicompartmental PKA in which both tibiofemoral compartments are replaced. In addition, implant 502 may be utilized to replace two compartments of the bone (i.e., one tibiofemoral compartment and the patellofemoral compartment) such that insert 504 is connected to femur 600 and articular component 512 overlies such insert 504. Alternatively, inserts 104 and 404 may be connected to the bone and articular component 512 may overly and be connected to inserts 104 and 404 such that inserts 104 and 404, while not directly connected to each other, are connected to each other indirectly via articular component 512.

Figure 7A:
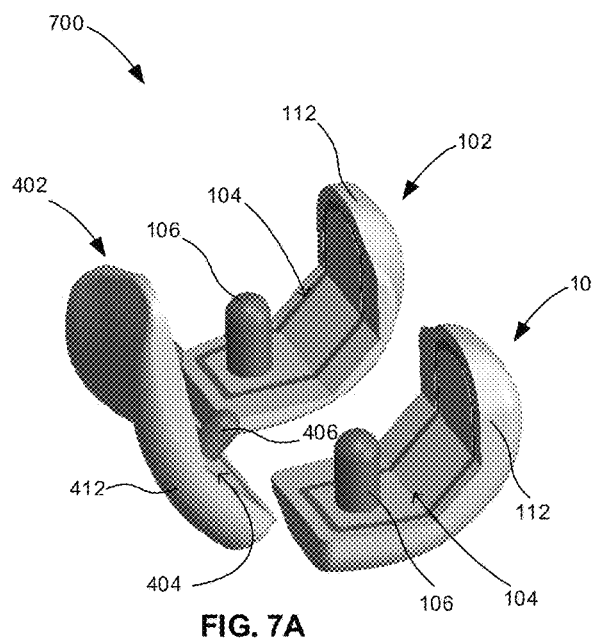
FIG. 7A is a perspective view of a system of implants according to one embodiment of the present invention.
Figure 7B:
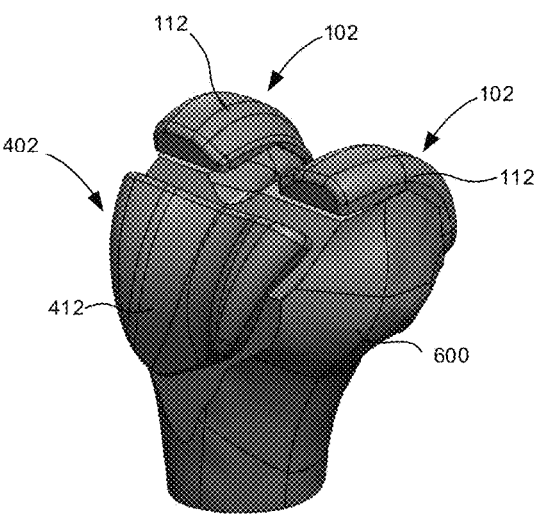
FIG. 7B is a perspective view of the system of implants of FIG. 7A connected to a resected femur.

FIGS. 7A and 7B illustrate a system 700 of inserts and articulating components that form a tricompartmental implant. System 700 includes two implant 102 and implant 402. As previously described, such implants 102 and 402 may be used in either unicompartmental or bicompartmental PKA. In addition, such implants 102 and 402 of system 700 can also form a tricompartmental implant, as shown in FIGS. 7A and 7B. In this regard, implants 102 form a medial condylar portion and a lateral condylar portion of the tricompartmental implant. In addition, implant 402 completes the tricompartmental implant by forming a patellofemoral portion thereof. Thus, system 700 provides for any combination of implants to achieve unicompartmental, bicompartmental, or tricompartmental knee arthroplasty. These implants, including their respective inserts, allows for a revision in which a unicompartmental implant is converted to a bicompartmental or tricompartmental, and a bicompartmental is converted to a tricompartmental. Such conversions may make use of an already implanted insert such that the already implanted insert need not be removed from the bone so as to avoid unnecessary bone loss. Alternatively, the configuration of insert and implant allows for a worn articular component to be swapped out without disturbing the underlying bone.

Thus in an exemplary method of use, a unicompartmental implant, such as implant 402 may have been implanted as the primary implant. In this regard, the bone in the primary procedure may have been resected and insert 404 may have been connected to the resected bone along with corresponding articular component 412. However, due to arthritic progression in the native cartilage in one or both of the tibiofemoral compartments after the primary procedure, or for some other reason, a revision procedure to a bicompartmental implant or tricompartmental implant may be necessary. In this regard, instead of removing the entirety of implant 402. Articular components 412 may be disconnected from its corresponding insert 404 via one of the techniques previously described (i.e., cutting the articular component 412 or using a tool to remove articular component 412) so as to preserve the bone underlying insert 404.

The diseased bone in the tibiofemoral compartments may then be resected while insert 404 remains in place. Once the bone is prepared, inserts 104 along with articular component 112 may be connected to the lateral and/or medial condyles so as to achieve one of the configurations depicted in FIG. 6C, 6E, or 7A. Alternatively, articular component 512 may be connected to an insert 104 and insert 404.

In another example, the patient might begin with unicompartmental implant 102, such as a lateral condyle as shown in FIG. 6A. Later, a revision might be necessary to add a second implant, such as implant 102 at the medial condyle or 402 at the anterior aspect of femur, as shown in FIG. 6C, to create a bicompartmental implant configuration. As the knee continues to wear, it may become necessary to create a tricompartmental implant, as shown in FIG. 7A. This can be achieved by adding an additional insert while leaving the other previously implanted inserts 104, 404 in place.

Figure 7C:
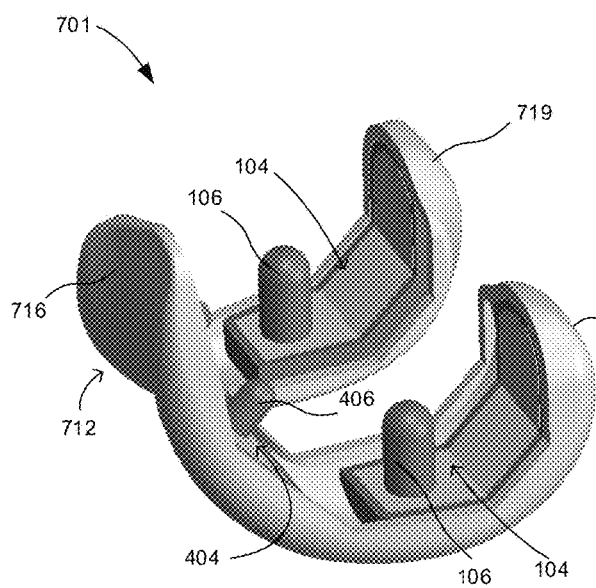
FIG. 7C is a perspective view of an implant according to an even further embodiment of the present invention.
Figure 7D:
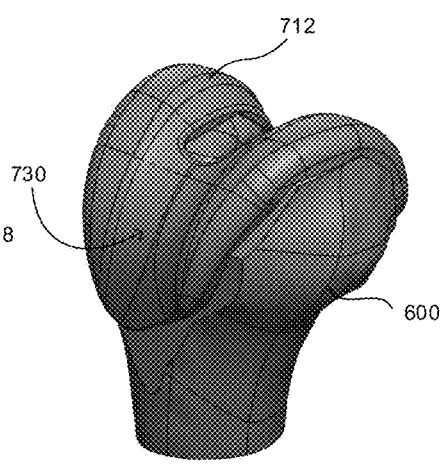
FIG. 7D is a perspective view of the implant of FIG. 7C connected to a resected femur.

Alternatively, instead of creating a tricompartmental implant of the type shown in FIGS. 7A and 7B, the surgeon may opt for a full articulation tricompartmental implant, as shown in FIGS. 7C and 7D. Such full articulation tricompartmental implant 701 includes an articular component 712 that includes lateral and medial condylar portions 718, 719 and an anterior flange portion 716 that are connected to each other to form a monolithic tricompartmental articular component 712. Thus, the surgeon may use inserts 104, insert 404, or even 504 in conjunction with articulating component 712.

Figure 8:
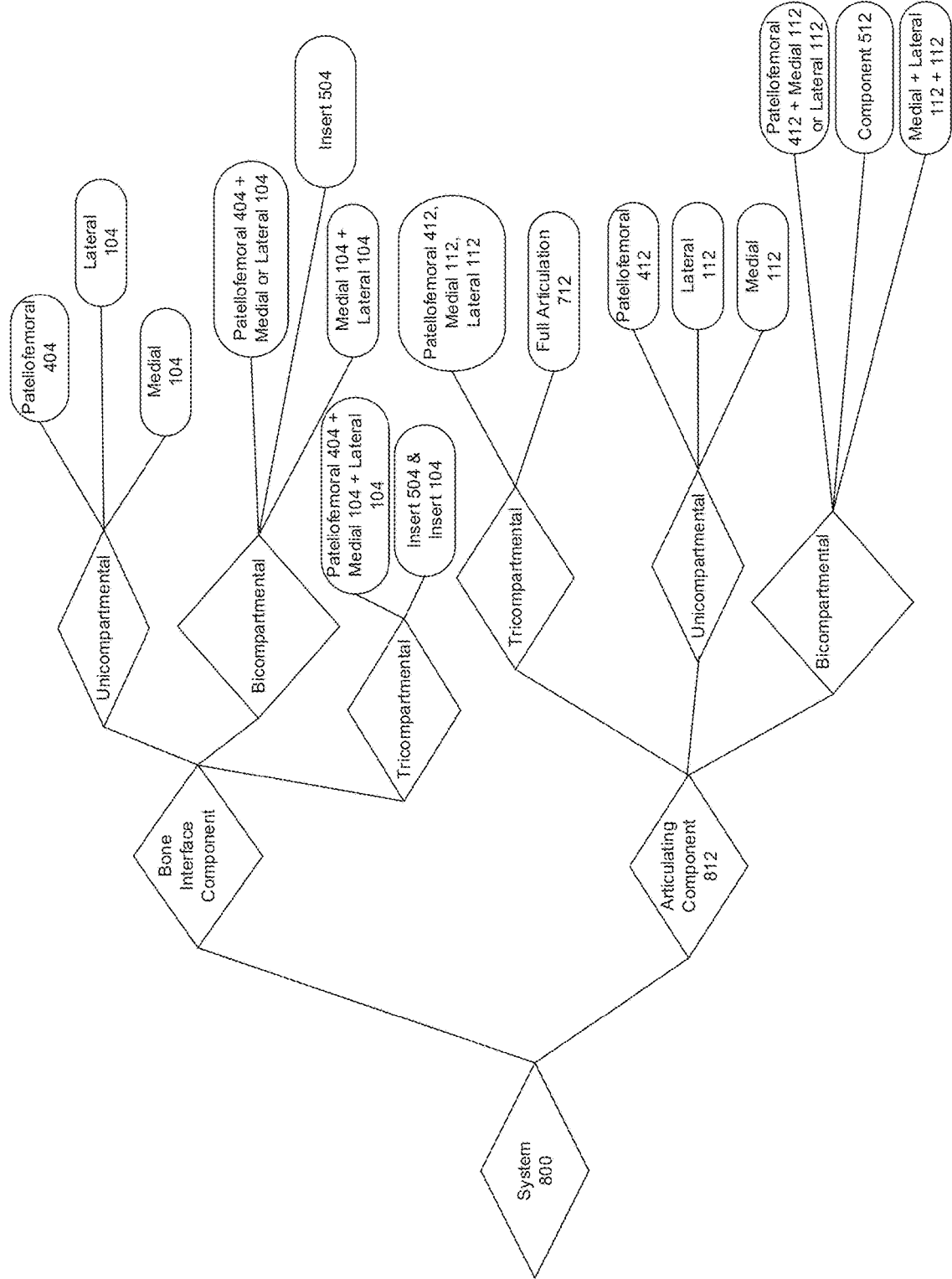
FIG. 8 is a flow diagram according to one embodiment of the present invention.

FIG. 8 illustrates a system 800 comprised of various bone interface component and articulating component combinations. In particular, for unicompartmental procedures, a patellofemoral bone interface component or insert 404 may be used with a patellofemoral articular component 412, a lateral bone interface component or insert 104 may be used with a lateral articular component 112, and a medial bone interface component or insert 104 may be used with a medial articular component 112.

For bicompartmental procedures, a patellofemoral bone interface component 404 in combination with a lateral or medial bone interface component 104 may be used with either component 512 or a combination of patellofemoral articular component 404 and medial/lateral articular component 104. Alternatively, where bone interface component or insert 504 is used, component 512 is used in conjunction therewith. Where the bicompartmental procedure includes medial and lateral bone interface components 112, medial and lateral articular components 112 are used therewith.

For tricompartmental procedures, a combination of patellofemoral bone interface component 404 and lateral and medial bone interface components 104 may be used in conjunction with either full articulation component 512 or a corresponding combination of patellofemoral articular component 412 and medial and lateral articular components 112.

Thus, any procedure can be performed to swap out used/worn articular components for new articular components without disturbing a well fixed bone interface component/insert and to convert one implant type/combination to another also without disturbing well fixed inserts and their underlying bone.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of converting a first joint prosthesis to a second joint prosthesis in-situ comprising:
    removing a first articulating component from a first bone interface component having been connected to a bone in a previous procedure such that the first bone interface component remains connected to the bone;
    connecting a second bone interface component to a resected portion of the bone; and
    connecting the first bone interface component and the second bone interface component via a second articulating component, wherein the second articulating component is sized and shaped to cover both the first and second bone interface components and span a distance therebetween,
    wherein the second articulating component includes an articulating surface configured to articulate with a third joint prosthesis, and
    wherein at least a portion of the second articulating component is in contact with the first and second bone interface components.

2. The method of claim 1, wherein each of the first and second bone interface components are made of a metal.

3. The method of claim 2, wherein the first and second bone interface components each include a bone contacting surface made of a porous metal.

4. The method of claim 1, wherein each of the first and second articulating components are made of a polymer.

5. The method of claim 1, further comprising implanting a third bone interface component to the resected portion of the bone.

6. The method of claim 5, further comprising connecting the third bone interface component to the first and second bone interface components via the second articulating component, wherein the second articulating component is sized and shaped to cover each of the first, second, and third bone interface components.

7. The method of claim 6, wherein the second articulating component is a tricompartmental femoral component that includes lateral and medial condyles for tibiofemoral articulation and an anterior flange having a trochlear groove for patellofemoral articulation.

8. The method of claim 1, wherein the second articulating component is a bicompartmental femoral component that includes an anterior flange defining a trochlear groove for patellofemoral articulation and either a lateral or medial condyle for unicondylar tibiofemoral articulation.

9. The method of claim 1, wherein removing the first articulating component further comprises cutting the first articulating component at a location adjacent to a locking mechanism, the locking mechanism coupling the first articulating component to the first bone interface component.

10. The method of claim 1, wherein connecting the first bone interface component and the second bone interface component further includes applying a force to the second articulating component to deform the second articulating component to snap-fit the second articulating component onto one or more locking mechanisms on the first and second bone interface components.

11. A method of converting a first joint prosthesis to a second joint prosthesis in-situ comprising:

removing a first articulating component from a first bone interface component such that the first bone interface component remains attached to a femur, the first bone interface component having been previously connected to the femur in a previous procedure;

connecting a second bone interface component to a resected portion of the femur; and connecting a second articulating component to the first and second bone interface components.

12. The method of claim 11, wherein the first articulating component includes a unicondylar component that has an articular surface that defines one of a lateral and medial condyle.

13. The method of claim 11, wherein the first articulating component includes a patellofemoral component that has an articular surface that defines a trochlear groove for patellofemoral articulation.

14. The method of claim 11, wherein the second articulating component includes a unicondylar component and a patellofemoral component such that the second articulating component is a bicompartmental component, and wherein connecting the second articulating component to the first and second bone interface components includes connecting the tibiofemoral component to the first or second bone interface component and connecting the unicondylar component to the other of the first and second bone interface components such that the unicondylar component and patellofemoral component are spaced apart from each other.

15. The method of claim 11, further comprising:

connecting a third bone interface component to the femur such that the first, second, and third bone interface components are each spaced apart from one another, and connecting the second articulating component to the third bone interface component.

16. The method of claim 15, wherein the second articulating component is a full-articulation tricompartmental component having lateral and medial condyles for tibiofemoral articulation and an anterior flange defining a trochlear groove for patellofemoral articulation.

17. The method of claim 15, wherein the second articulating component includes first and second unicondylar components and a patellofemoral component, and wherein connecting the second articulating component to the first, second, and third bone interface components includes separately connecting the first and second unicondylar components and patellofemoral component to any of the first, second, and third bone interface components not occupied by one of the other unicondylar or patellofemoral components.

18. The method of claim 11, wherein the removing step includes cutting off a portion of the first articulating component from the first bone interface component.

* * * * *